United States Patent [19]
Anderson

[11] 3,939,700
[45] Feb. 24, 1976

[54] MATERIAL HARDNESS TESTER
[75] Inventor: Clifford E. Anderson, Stratford, Conn.
[73] Assignee: American Chain & Cable Company, Inc., Bridgeport, Conn.
[22] Filed: Aug. 15, 1972
[21] Appl. No.: 280,875

[52] U.S. Cl. .................................................. 73/83
[51] Int. Cl.² ........................................... G01N 3/44
[58] Field of Search ........ 73/83, 81, 78, 85, 141 AB

[56] References Cited
UNITED STATES PATENTS

| | | |
|---|---|---|
| 2,520,387 | 8/1950 | Dobry et al. ............................ 73/81 |
| 2,667,065 | 1/1954 | Ernst ..................................... 73/81 |
| 2,667,066 | 1/1954 | Ernst ..................................... 73/81 |
| 3,182,491 | 5/1965 | Tschirf et al. ........................... 73/83 |
| 3,309,916 | 3/1967 | Pearson ................................ 73/81 |
| 3,367,174 | 2/1968 | Affri ..................................... 73/83 |

*Primary Examiner*—Richard C. Queisser
*Assistant Examiner*—Stephen A. Kreitman
*Attorney, Agent, or Firm*—Pennie & Edmonds

[57] ABSTRACT

An improved tester for measuring the hardness of materials, the tester having multiple spring means and an adjustable control for placing one or both of the spring means into operation to load the tester under different minor loads.

6 Claims, 1 Drawing Figure

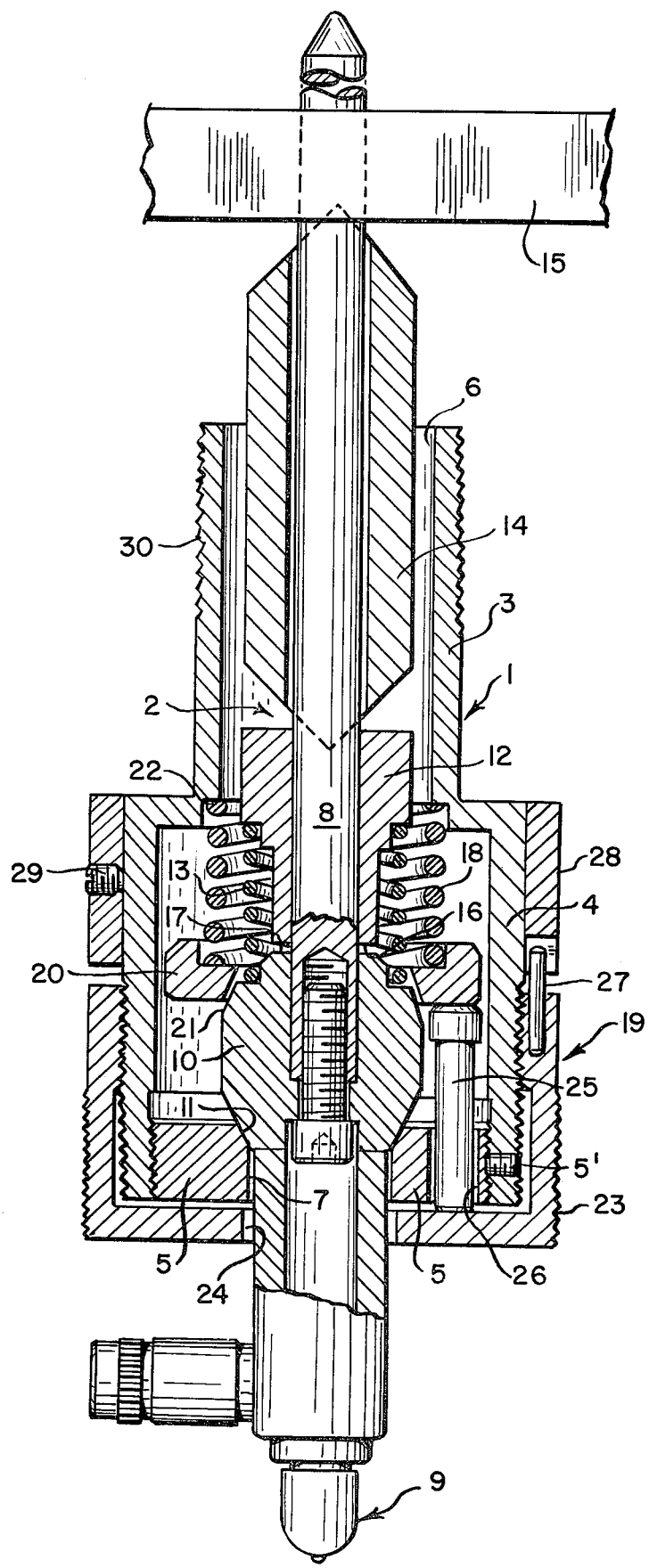

MATERIAL HARDNESS TESTER

BACKGROUND OF THE INVENTION

In the conventional Rockwell tester as used for measuring the hardness of materials, the tester is first loaded against the workpiece under a minor load. A reading of the depth of indentation is taken under the minor load; and the tester is then loaded under a major load. After release of the major load, a new reading is taken for comparison with the first reading. Using the regular Rockwell scales, the hardness of the material can thus be determined. With workpieces of substantial thickness, the Rockwell tester is conventionally loaded to a 10 kg. minor load.

When measuring the described of materials which are quite thin, the same procedure descirbed above is used. However, the usual minor load to which the tester is loaded is only 3 kg. and Rockwell superficial scales are used to take a reading of the hardness of the material. Most often, separate testers are required for measuring materials where different Rockwell scales are used. This is because the testers are constructed with internal spring mechanisms for loading at one specified minor load.

Multiple purpose testers have been constructed which are capable of applying either 3 or 10 kg. minor loads. Testers of this type use the weight of the lever arm structure of the tester for applying a 3 kg. minor load, while the 10 kg. minor load is applied by adding external weights. The major problem with this type of system lies in the fact that should any force impede the action of the lever arm, the minor load will be invalid. For this reason, means must be included for applying the major loads without disturbing the lever arm. This, in turn, requires considerable alteration of a standard tester in converting it to one capable of applying different minor loads.

SUMMARY OF THE INVENTION

In accordance with the teachings of the present invention, a minor loading system has been developed for loading the tester to either of two minor loads. A standard Rockwell hardness tester can be converted to a multiple tester by simply replacing the plunger unit of the standard equipment with a modified plunger unit. The improved tester generally includes two separate spring systems for loading the plunger. One of the springs loads the plunger rod of the tester to a 3 kg. minor load. The second spring adds 7 kgs. to the load to provide a 10 kg. loading. An adjustable control is provided for selectively removing the 7 kg. spring load from the system. The improved tester of the present invention offers the advantage of standardization. Merely replacing the plunger unit of a standard tester is all that is needed to convert it to a multiple tester. There is no longer any need for special castings, lever arms, mechanisms or other parts. In addition, the improved tester of the present invention is simple and easy to maintain.

BRIEF DESCRIPTION OF THE DRAWING

FIG. 1 is a cross-sectional view of the plunger unit of a hardness tester showing the present invention.

DETAILED DESCRIPTION OF THE PREFERRED EMBODIMENT

FIG. 1 shows the plunger unit of a material hardness tester as generally including a housing 1 and internal plunger means 2. The housing is constructed of a sleeve 3 having an enlarged lower skirt portion 4. A disc member 5 is threadedly attached to the lower end of the skirt portion and held in place by a set screw 5. The upper and lower ends of the housing are provided with openings 6 and 7, respectively; the lower opening being formed in the disc member 5.

The plunger 2 includes a plunger rod 8 slidably disposed within the housing and extending through the opposite openings 6 and 7. An indenter mechanism 9 is attached to the lower end of the plunger. The plunger rod has an intermediate enlarged portion 10 disposed internally of the housing. This enlarged portion is adapted to seat against a seating surface 11 formed on the disc member 5 adjacent to lower opening 7.

Disposed above the enlarged portion is a seating collar member 12. This member is loosely positioned on the plunger rod for axially sliding movement relative thereto. As shown in FIG. 1, the upper end of the seating collar is enlarged. A first compression spring 13 is positioned between this enlarged end and the enlarged portion 10 of the plunger rod.

A knife-edge member 14 is also slidably mounted on the plunger rod. This member is positioned above the seating collar and normally rests on it. The upper end of the knife-edge member engages against the conventional lever arm mechanism 15 of the hardness tester which is used in connection with applying the major loads.

The structure of the tester so far described is conventional and operates as follows. The workpiece, the hardness of which is to be measured, is brought up into engagement with the indenter 9. This causes the plunger rod to become unseated from the seating surface 11. Upward movement continues for a prescribed distance to load the tester to the spring load of the spring 13. The spring loading is accomplished due to the fact that the spring 13 is backed up against the seating collar 12 which in turn is held against axial movement by the knife-edge member 14 engaging between the seating collar and the overlying lever 15.

After the minor load has been applied to the workpiece, the lever 15 is caused to pivot to force the knife-edge member and seating collar downwardly. When the lower end 16 of the seating collar engages against the upper surface 17 of the enlarged portion 10 of the plunger rod, further downward movement of the lever arm will cause the plunger to move downwardly. This movement is continued until the major load is produced. The major load is then removed and the readings of the initial minor load and the final loading are compared on the appropriate Rockwell hardness scale to determine the hardness of the material.

In accordance with the teachings of the present invention, the spring 13 produces a 3 kg. minor load; this loading being appropriate for measuring the hardness of thin materials. In addition to the spring 13, a second compression spring 18 is provided. When operative, this spring will produce a 7 kg. loading of the tester which when added to the 3 kg. loading of the spring 13, provides a combined minor load of 10 kg. This load is suitable for measuring the hardness of thicker materials.

The loading produced by the second spring 18 is adapted to be selectively removed from the system. For this purpose, a control means, generally designated by reference numeral 19, is provided. This control means includes an annular collar 20 seated on the side of the enlarged portion 10 of the plunger rod, opposite the opening 7 of the housing; that is, it is seated on the upper surface 21.

The second spring means 18 has one end supported by the upper surface of the collar 20 and its other end engages against a seating surface 22 formed in the housing. As shown in FIG. 1, this seating surface 22 is disposed on the side of the collar 20 facing away from the enlarged portion 10 of the plunger rod. The distance between the annular collar 20 and the seating surface 22 is such that the spring 18 will be under compression.

The control means for selectively placing the second spring into the loading system further includes an adjusting nut 23. The adjusting nut is threaded onto the skirt portion 4 of the housing in covering relation with the lower opening 7 of the housing. The adjusting nut includes its own opening 24 aligned with the opening 7 for permitting passage of the plunger rod 8 therethrough. The adjusting nut is attached to move axially of the plunger rod by turning it in one or the other direction.

Drive means in the form of a plurality of drive pins 25 are disposed between the adjusting nut and the annular collar. There are three drive pins spaced equally about the plunger rod. Only one of the pins is shown in FIG. 1. The lower end of each of the drive pins is supported by the adjusting nut while the upper end of each pin engages against the lower surface of the annular collar 20. To permit this engagement with the collar, the collar is constructed to extend laterally beyond the enlarged portion 10 of the plunger rod. The disc member 5 is provided with openings 26 for receiving the drive pins.

In the position of the elements shown in FIG. 1, the tester is set for producing a minor load of 3 kg., the spring 13 being the only one operative in the loading system. When it is desired to add the 7 kg. loading of the spring 18, the adjusting nut is turned to lower it on the skirt portion 4 of the housing. This lowers the drive pins 25 and permits the annual collar to drop until it seats on the surface 21 of the enlarged portion 10 of the plunger. Further turning will lower the drive pins out of engagement with the annular collar and thus the spring 18 will be operatively connected into the loading system to add its loading to that of the spring 13. Turning of the adjusting nut in the opposite direction will have the effect of returning the elements of the system to the positions shown in FIG. 1 wherein just the spring 13 is operative.

For full control, it is only necessary to rotate the adjusting nut for about 90°. To limit the turning of the adjusting nut, a stop pin 27, is fixed to its upper end and extends into a slot in the housing part 28. Part 28 is fixed to the skirt portion 4 by a set screw 29 and is slotted for 90°.

The entire mechanism shown in FIG. 1 is adapted to be used in the conventional Rockwell tester in substitution for the conventional plunger unit. For this purpose, the housing 1 is threaded at 30 for attachment in the apparatus in the same way as the conventional plunger unit.

I claim:

1. In a material hardness tester having an apparatus for applying a major and a minor load including a housing, a plunger assembly having a plunger rod slidably secured in said housing, and a first spring means operatively connected to said plunger rod for urging it axially in one direction under a first predetermined spring load for applying a first minor load, the improvement comprising:
   a. second spring means adapted to be operatively connected to said plunger rod for urging it axially in said one direction under a second predetermined spring load for applying a second minor load different than said first minor load;
   b. control means for selectively removing the second spring means from operative connection with a plunger rod to selectively permit loading of the plunger rod under said first spring load alone and under said first and second spring loads together such that either minor load can be applied independently of the other; and
   c. said plunger assembly including means, with said spring means and said control means, for replacing a plunger assembly of a standard hardness tester to convert the standard tester to a multiple tester.

2. The improvement in the material hardness tester as set forth in claim 1 wherein said first minor load is 10 kilograms and second said minor load is 3 kilograms.

3. In a material hardness tester having a housing, a plunger rod extending through openings in opposite ends of said housing and having an enlarged portion disposed within the housing, seating means adjacent one of said openings upon which said enlarged portion is adapted to seat to limit axial movement of the plunger rod in one direction through said one opening, and first spring means engaging against said enlarged portion for urging the plunger rod axially in said one direction under a first predetermined spring load, the improvement comprising:
   a. second spring means for engaging against said enlarged portion of the plunger rod for urging the plunger rod axially in said one direction under a second predetermined spring load; and
   b. control means for selectively removing the second spring means from engagement with the enlarged portion of the plunger rod to selectively permit loading of the plunger rod under said first spring load alone and said first and second spring loads together, said control means including:
      i. an annular collar seated on the enlarged portion of the plunger rod on the side thereof opposite the one opening in said housing;
      ii. means for supporting one end of said second spring means on said collar to load said plunger rod under said second spring load; and
      iii. adjustable means for selectively raising the annular collar off of the enlarged portion of the plunger rod to remove the second spring load from said plunger rod.

4. The improvement in the material hardness tester as set forth in claim 3 wherein said control means further comprises:
   a. means for seating the other end of the second spring means against the housing on the side of the collar facing away from the enlarged portion of the plunger rod to hold the spring under compression against said collar.

5. In a material hardness tester having a housing, a plunger rod extending through openings in opposite ends of said housing and having an enlarged portion disposed within the housing, seating means adjacent one of said openings upon which said enlarged portion is adapted to seat to limit axial movement of the plunger rod in one direction through said one opening, and first spring means engaging against said enlarged portion for urging the plunger rod axially in said one direction under a first predetermined spring load, the improvement comprising:
  a. second spring means for engaging against said enlarged portion of the plunger rod for urging the plunger rod axially in said one direction under a second predetermined load; and
  b. control means for selectively removing the second spring means from engagement with the enlarged portion of the plunger rod to selectively permit loading of the plunger rod under said first spring load alone and said first and second spring loads together, said control means including:
    i. an annular collar seated on the enlarged portion of the plunger rod on the side thereof opposite the one opening in said housing;
    ii. means for seating the other end of the second spring means against the housing on the side of the collar facing away from the enlarged portion of the plunger rod to hold the spring under compression against said collar;
    iii. means for supporting one end of said second spring means on said collar to load said plunger rod under said second spring load;
    iv. adjustable means for selectively raising the annular collar off of the enlarged portion of the plunger rod to remove the second spring load from said plunger rod;
    v. an adjusting nut threadedly attached to the housing in covering relation to said one opening for movement axially of the plunger rod, said nut having an opening with the one opening through which said plunger rod extends; and
    vi. drive means supported by the adjusting nut and disposed between the adjusting nut and the annular collar for raising said collar off of the enlarged portion of the plunger rod upon threading of the adjusting nut along the housing.

6. The improvement in the material hardness tester as set forth in claim 5 wherein: outwardly
  a. the annular collar extends laterally beyond the enlarged portion of the plunger; and
  b. the drive means includes drive pins engaging against the side of the collar facing said one opening laterally outwarrdly of the enlarged portion of the plunger rod.

* * * * *

UNITED STATES PATENT AND TRADEMARK OFFICE
CERTIFICATE OF CORRECTION

PATENT NO. : 3,939,700

DATED : February 24, 1976

INVENTOR(S) : Clifford E. Anderson

It is certified that error appears in the above-identified patent and that said Letters Patent are hereby corrected as shown below:

Column 1, line 17, "the described of materials" should read --the hardness of materials--.

Column 6, line 20, "wherein: outwardly" should read --wherein:--;

line 25, "outwarrdly" should read --outwardly--.

Signed and Sealed this

Third Day of August 1976

[SEAL]

Attest:

RUTH C. MASON
Attesting Officer

C. MARSHALL DANN
Commissioner of Patents and Trademarks